(12) United States Patent
Sharifi et al.

(10) Patent No.: US 7,803,134 B2
(45) Date of Patent: Sep. 28, 2010

(54) SYRINGE ASSEMBLY AND INFUSION PUMP ASSEMBLY INCORPORATING SUCH

(75) Inventors: Bahram Sharifi, Schwenksville, PA (US); Patrick Paul, Boca Roton, FL (US); William Lawson, IV, Trappe, PA (US)

(73) Assignee: Animas Corporation, West Chester, PA (US)

( * ) Notice: Subject to any disclaimer, the term of this patent is extended or adjusted under 35 U.S.C. 154(b) by 658 days.

(21) Appl. No.: 11/651,876

(22) Filed: Jan. 10, 2007

(65) Prior Publication Data

US 2008/0167618 A1    Jul. 10, 2008

(51) Int. Cl.
*A61M 37/00*    (2006.01)
(52) U.S. Cl. .................. 604/155; 604/151; 604/154
(58) Field of Classification Search ......... 604/131–157, 604/187–240, 890, 891.1, 403, 43, 30, 93.01, 604/257; 128/DIG. 1
See application file for complete search history.

(56) References Cited

U.S. PATENT DOCUMENTS

| | | | |
|---|---|---|---|
| 2,629,376 A | 7/1949 | Gallice et al. | |
| 2,756,748 A | 1/1952 | Ferguson | |
| 2,895,773 A | 7/1959 | McConnaughey | |
| 3,151,617 A * | 10/1964 | Baum | 604/222 |
| 3,540,760 A | 11/1970 | Miller et al. | |
| 3,987,940 A | 10/1976 | Tischlinger | |
| 4,030,496 A | 6/1977 | Stait et al. | |
| 4,030,498 A | 6/1977 | Tompkins | |
| 4,655,462 A | 4/1987 | Balsells | |
| 4,773,900 A | 9/1988 | Cochran | |
| 5,062,830 A | 11/1991 | Dunlap | |
| 5,085,638 A * | 2/1992 | Farbstein et al. | 604/110 |
| 5,741,232 A | 4/1998 | Reilly et al. | |
| 5,782,815 A | 7/1998 | Yanai et al. | |
| 5,873,861 A | 2/1999 | Hitchins et al. | |
| 5,944,694 A | 8/1999 | Hitchins et al. | |
| 5,947,929 A | 9/1999 | Trull | |
| 5,947,935 A | 9/1999 | Rhinehart et al. | |
| 5,993,423 A | 11/1999 | Choi | |
| 6,090,064 A | 7/2000 | Reilly et al. | |
| 6,248,093 B1 | 6/2001 | Moberg | |
| 6,287,521 B1 * | 9/2001 | Quay et al. | 422/101 |
| 6,413,238 B1 | 7/2002 | Maget | |
| 6,425,885 B1 | 7/2002 | Fischer et al. | |
| 6,652,489 B2 | 11/2003 | Trocki et al. | |
| 6,656,148 B2 | 12/2003 | Das et al. | |
| 6,659,980 B2 | 12/2003 | Moberg et al. | |
| 6,733,475 B2 * | 5/2004 | Huang et al. | 604/110 |
| 6,800,071 B1 | 10/2004 | McConnell et al. | |
| 6,854,620 B2 | 2/2005 | Ramey | |

(Continued)

FOREIGN PATENT DOCUMENTS

DE    20011366 U1    10/2000

(Continued)

*Primary Examiner*—Nicholas D Lucchesi
*Assistant Examiner*—Leah Stohr

(57) ABSTRACT

A syringe assembly for use with an infusion pump having a drive piston. The syringe assembly comprises a substantially hollow syringe housing and a plunger axially movable within the syringe housing to dispense a fluid therefrom. The plunger has a body with a portion thereof configured to engage a radially elastic member associated with the drive piston such that the plunger is releasably axially secured relative to the drive piston.

7 Claims, 5 Drawing Sheets

U.S. PATENT DOCUMENTS

| | | |
|---|---|---|
| 7,000,806 B2 | 2/2006 | Py et al. |
| 7,008,403 B1 | 3/2006 | Mallett |
| 7,025,226 B2 | 4/2006 | Ramey |
| 7,029,458 B2 | 4/2006 | Spohn et al. |
| 7,033,338 B2 | 4/2006 | Vilks et al. |
| 7,041,081 B2 | 5/2006 | Minezaki et al. |
| 7,041,082 B2 | 5/2006 | Blomquist et al. |
| 2001/0034502 A1* | 10/2001 | Moberg et al. ............... 604/154 |
| 2003/0163089 A1 | 8/2003 | Bynum |
| 2003/0163090 A1 | 8/2003 | Blomquist et al. |
| 2004/0158205 A1* | 8/2004 | Savage ....................... 604/151 |

FOREIGN PATENT DOCUMENTS

| | | |
|---|---|---|
| EP | 1 570 875 A1 | 9/2005 |
| WO | WO 02/04049 A1 | 1/2002 |
| WO | WO 2004/103429 A2 | 12/2004 |
| WO | WO 2005/094923 A1 | 10/2005 |

* cited by examiner

SYRINGE ASSEMBLY AND INFUSION PUMP ASSEMBLY INCORPORATING SUCH

FIELD OF THE INVENTION

The present invention relates to an infusion pump assembly for controlled delivery of a pharmaceutical product to a subject, and more specifically to a syringe assembly for use with the infusion pump.

BACKGROUND OF THE INVENTION

Infusion pumps provide a significant lifestyle benefit for individuals requiring multiple deliveries of volumetrically proportioned medication to their body over a period of time. Infusion pumps reliably dispense the required medication to the patient through an infusion path established between the patient and the pump. The infusion path is a conduit secured to the pump system at one end and secured intravenously or subcutaneously to a patient on the other. The operation of the infusion pump is controlled by a processor. The processor controls the delivery of periodic dosages of medication to a patient at predetermined times. Thus, a patient is able to rely on the infusion pump for delivering the required dosage of medication intravenously or subcutaneously over a period of time. In this way, the patient need not interrupt life activities for repeated manual delivery of required medication.

As is known, infusion pumps often employ a piston-type drive mechanism for urging the contents of a pharmaceutical cartridge or "syringe assembly" internal to the pump along the infusion path to the subject. The piston-type drive selectively drives the syringe plunger to dispense a desired amount of fluid from the syringe housing.

SUMMARY OF THE INVENTION

The features and advantages of the invention will be set forth in the description which follows, and in part will be apparent from the description, or may be learned by practice of the invention. The advantages of the invention will be realized and attained by the apparatus, and the method of practicing the invention, particularly pointed out in the written description and claims below, as well as in the attached drawings.

In accordance with an aspect of the invention, a syringe assembly for use with an infusion pump having a drive piston is provided. The syringe assembly comprises a substantially hollow syringe housing and a plunger axially movable within the syringe housing to dispense a fluid therefrom. The plunger has a body with a portion thereof configured to engage a radially elastic member associated with the drive piston such that the plunger is releasably axially secured relative to the drive piston.

In accordance with another aspect of the invention, an infusion pump assembly is provided. The infusion pump assembly comprises an insulin pump including a drive piston having a radially elastic member associated therewith, and a syringe assembly. The syringe assembly includes a substantially hollow syringe housing and a plunger axially movable within the syringe housing to dispense a fluid therefrom, the plunger having a body with a portion configured to engage the radially elastic member associated with the drive piston such that the plunger is releasably axially secured relative to the drive piston.

In accordance with another aspect of the invention, the drive piston has a first annular groove and the plunger has a second annular groove. The radially elastic member is positional within the first and second grooves to releasably, axially secure the plunger relative to the drive piston.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown various embodiments. It should be understood, however, that the invention is not limited to the precise arrangements and instrumentalities shown.

In the drawings.

DETAILED DESCRIPTION OF THE INVENTION

Figure 1:
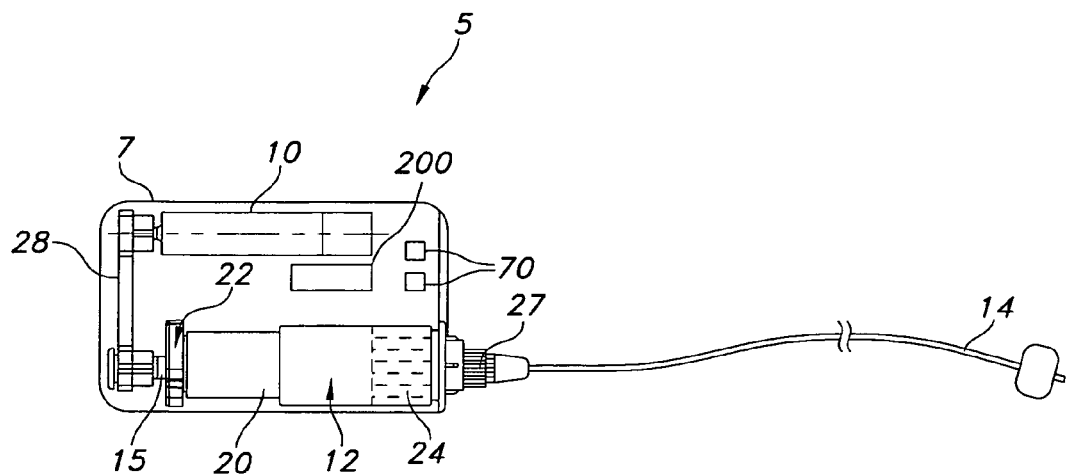
FIG. 1 is side elevation view of an exemplary infusion pump incorporating an embodiment of the present invention, the infusion pump having a wall of its casing removed to show the layout of the components therein.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the infusion pump and designated parts thereof. The terminology includes the words specifically mentioned above, derivatives thereof and words of similar import.

Referring to FIG. 1, piston-type infusion pump 5 in accordance with an exemplary embodiment of the present invention is shown for delivering medication 24 or other fluid (in phantom) to a patient along infusion path 14. Infusion pump 5 desirably includes sealed pump casing 7, processing circuitry 200, power cells 70, motor 10, gear train 28, lead screw 15, and drive piston 22. Syringe assembly 12 is positional within pump casing 7 such that drive piston 22 engages plunger 20 of syringe assembly 12.

In operation, processing circuitry 200, powered by power cells 70, controls the operation of infusion pump 5. Motor 10 is incrementally engaged to infuse medication to a patient at predetermined intervals. Upon engagement, motor 10 causes lead screw 15 to rotate by means of gear train 28. When lead screw 15 is driven by motor 10, drive piston 22 is driven axially toward syringe assembly 12, thereby pushing plunger 20. This causes delivery of medication 24 from within syringe housing 26 of syringe assembly 12. Infusion path 14 is connected by connector 27 to dispensing tip 25 (see FIG. 5) of syringe housing 26 to provide fluidic communication between infusion pump 5 and a patient.

Figure 2:
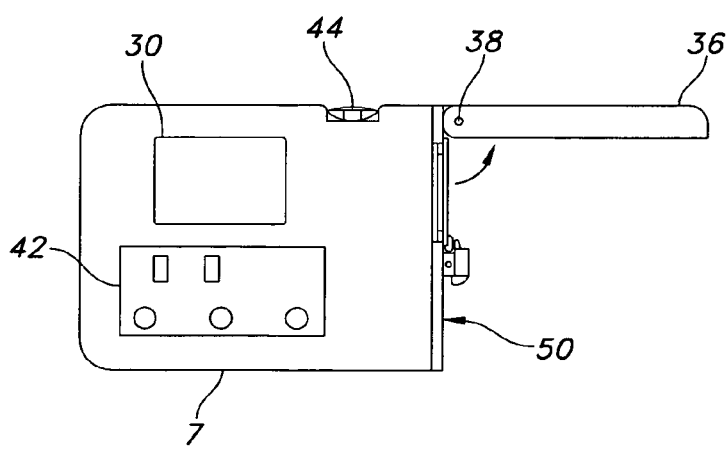
FIG. 2 is a side elevation view of the infusion pump shown in FIG. 1 with the wall in place and the pump door open.
Figure 3:
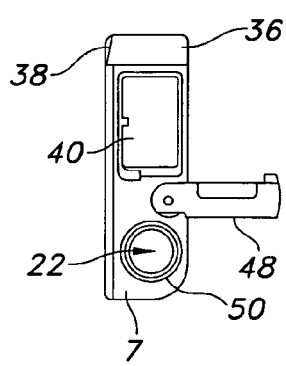
FIG. 3 is an end elevation view of the infusion pump with the pump door open for loading a syringe assembly.

Referring now to FIGS. 2-3, casing 7 of infusion pump 5 is shown. Pump casing 7 is desirably formed of a thermoplastic material and preferably made watertight by sealing any openings therein. Desirably, pump casing 7 supports LCD display 30, keypad 42, priming button 44, battery door 40, hinge 38, pump door latch 48, and pump door 36. To load a syringe assembly 12 within casing 7 pump door 36 is opened to expose the interior infusion port 50 and battery door 40. Syringe assembly 12 is configured to be moved axially through interior infusion port 50 into the interior of pump casing 7 such that plunger 20 axially engages drive piston 22, as will be described in more detail hereinafter. In FIGS. 2 and 3, pump door latch 48 has been rotated away from pump casing 7 in order to release pump door 36 so it may pivot open at hinge 38. Battery door 40 is removable for replacing the power cells 70.

The present invention is not limited to the illustrated infusion pump. Infusion pump 5 may have various configurations including various controls, power sources, drive means, access ports and doors, sizes and shapes.

Figure 4:
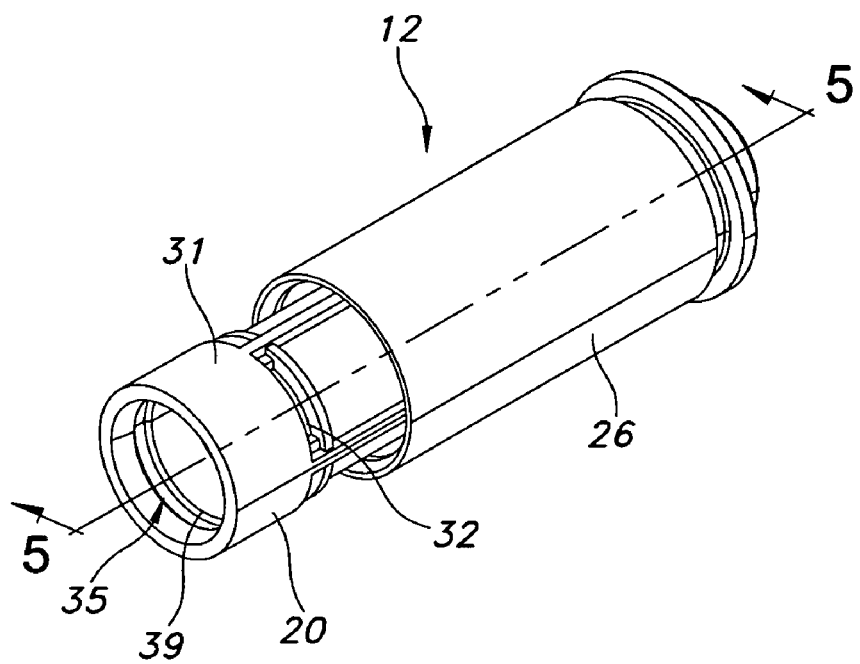
FIG. 4 is an isometric view of a syringe assembly in accordance with an exemplary embodiment of the present invention.
Figure 5:
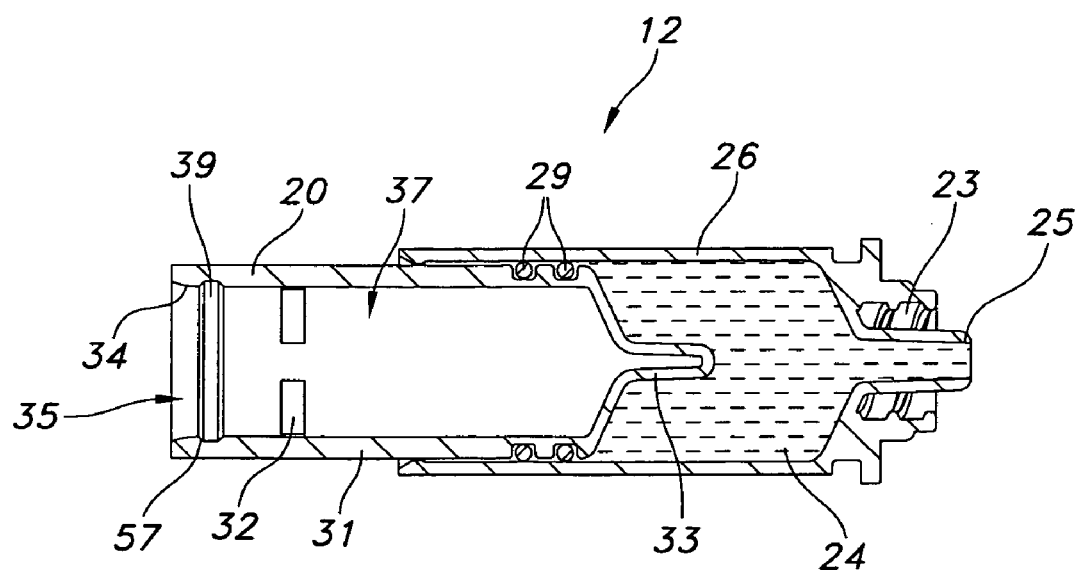
FIG. 5 is a cross-sectional view along the line 5-5 in FIG. 4.

Referring to FIGS. 4 and 5, syringe assembly 12 includes plunger 20 and syringe housing 26. Seal rings 29 or the like are provided between plunger 20 and syringe housing 26 to seal medication 24 within syringe housing 26. Seal rings 29 also provide a friction force between plunger 20 and syringe housing 26. This friction force axially secures plunger 20 relative to syringe housing 26 such that an axial force on plunger 20 that is greater than the friction force is required to move plunger 20 relative to syringe housing 26. As described hereinafter, drive piston 22 is configured to selectively move plunger 20 axially inward relative to syringe housing 26, which is axially fixed in place by door 36 of casing 7, such that medication 24 is dispensed through dispensing tip 25. Connection interface 23 is provided adjacent dispensing tip 25 to facilitate connection to connector 27. Various connection interfaces 23 may be provided.

In the present embodiment, plunger 20 includes tubular body 31 which has a generally hollow interior 37 extending between closed end 33 and generally open end 35. Generally open end 35 is configured to receive drive piston 22 as will be described hereinafter. Plunger body 31 may include vent holes 32 or the like to allow pressure to escape as drive piston 22 is advanced into hollow interior 37. Interior annular groove 39 is provided along the interior surface of plunger body 31 and is configured to receive a radially elastic member as described hereinafter to axially secure plunger 20 relative to drive piston 22. Interior annular groove 39 is desirably provided adjacent generally open end 35, but may otherwise be positioned. Syringe assembly 12 as illustrated in FIGS. 4 and 5 is pre-filled with medication 24 or the like and is ready for use in infusion pump 5.

Figure 6:
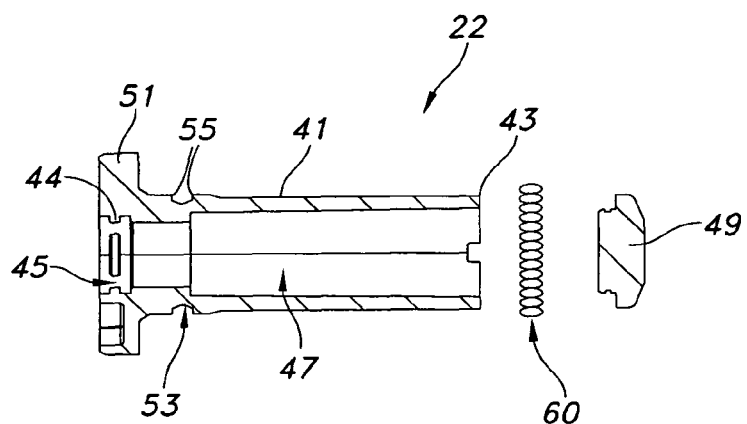
FIG. 6 is an exploded cross-sectional view of a drive piston in accordance with an exemplary embodiment of the invention.
Figure 7:
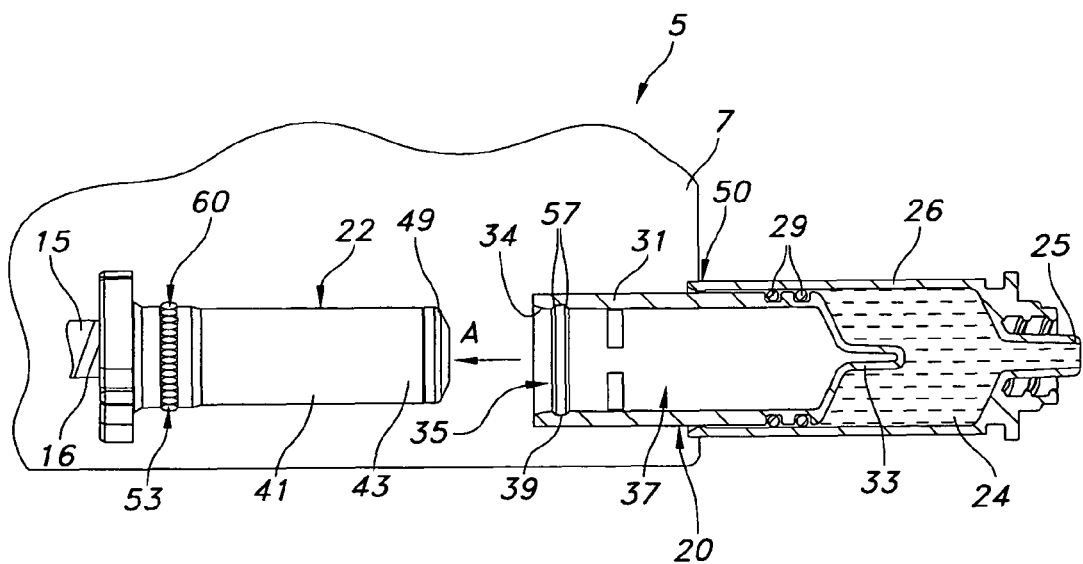
FIG. 7 is a side elevation view in partial section illustrating insertion of the syringe assembly into the infusion pump casing.

Referring to FIGS. 6 and 7, drive piston 22 includes tubular body 41 having a hollow interior portion 47 which is configured to receive lead screw 15. Threads 44 adjacent open end 45 of piston body 41 are configured to engage threads 16 of lead screw 15 to facilitate driving motion of drive piston 22. Drive piston 22 is supported within casing 7, either by lead screw 15 alone or via other support structures (not shown). Shoulder 51 may be provided about open end 45 to further support drive piston 22 within casing 7. End 43 of piston body 41 is configured to receive cap 49 which is desirably manufactured from an elastomeric material. Alternatively, end 43 may be manufactured as a closed end or cap 49 may be formed integrally therewith, for example, via overmolding.

Figure 8:
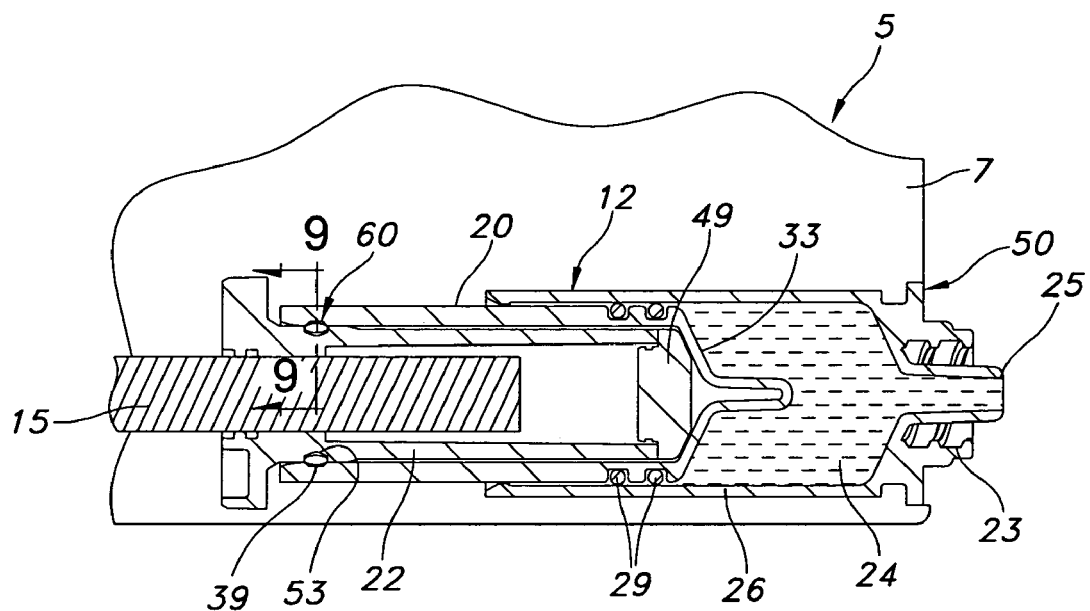
FIG. 8 is a cross-sectional view illustrating the syringe assembly of FIG. 7 loaded in an operational position within the infusion pump.

Exterior annular groove 53 is provided about piston body 41 and is configured to receive and retain radially elastic member 60. To assist in retaining radially elastic member 60 therein, exterior annular groove 53 desirably has flattened sides 55 extending generally parallel to one another. Exterior annular groove 53 is desirably positioned toward open end 45, but may be otherwise positioned. Referring to FIG. 8, interior annular groove 39 and exterior annular groove 53 are desirably axially aligned when syringe assembly 12 is fully installed in infusion pump 5 and cap 49 contacts plunger closed end 33.

As illustrated in FIG. 7, to install syringe assembly 12 within infusion pump 5, syringe assembly 12 is moved axially through interior infusion port 50, as indicated by arrow A. End 43 of drive piston 22 enters plunger 20 through open end 35 and passes through hollow interior 37 until cap 49 engages closed end 33. As radially elastic member 60 enters through plunger open end 35, radially elastic member 60 compresses such that radially elastic member 60 enters into the hollow interior 37. To assist such compression, inward taper 34 is desirably provided about open end 35. As radially elastic member 60 axially aligns with interior annular groove 39, radially elastic member 60 radially expands and engages interior annular groove 39, thereby axially securing plunger 20 relative to drive piston 22. Radially elastic member 60, inward taper 34 and interior annular groove 39 are desirably configured such that the insertion force required to insert and operatively engage plunger 20 with drive piston 22 is less than the friction force between plunger 20 and syringe housing 26 such that plunger 20 does not move relative to syringe housing 26 during insertion.

With radially elastic member 60 engaged between plunger 20 and drive piston 22, which is controllably axially fixed within casing 7, radially elastic member 60 provides an additional force against axial movement of plunger 20 relative to syringe housing 26. As such, a total force, equal to the friction force plus the elastic member additional force, axially secures plunger 20 relative to syringe housing 26. However, since the elastic member additional force is provided between drive piston 22 and plunger 20, this additional force does not have to be overcome to drive plunger 20 axially inwardly to dispense medication. As such, a more secure positioning between plunger 20 and syringe housing 26 is achieved without requiring a greater drive force.

Alternatively, since the total force includes the elastic member additional force, a reduced friction force may be utilized while still maintaining a desired total force. For example, a prior art system including a seal ring configured to provide a friction force of 2 lbs. between plunger 20 and syringe housing 26 would have a total force of 2 lbs. In an illustrative example of the present invention, elastic member 60, drive piston 22 and plunger 20 are configured such that elastic member 60 provides an additional force of 0.5 lbs. As such, to achieve the same total force, the friction force provided by seal rings 29 between plunger 20 and syringe housing 26 only needs to be 1.5 lbs. Therefore, the total force securing plunger 20 relative to syringe housing 26 remains the same, but the required drive force, i.e., the axial force required to overcome the friction force, is reduced from 2 lbs. to 1.5 lbs. The pump system may be operated more efficiently due to the reduction in the required drive force.

When syringe assembly 12 is to be removed, an axial force opposite arrow A is applied to syringe assembly 12. Radially elastic member 60 again compresses and disengages from interior annular groove 39. To facilitate such, it is desirable that at least rear edge of annular groove 39 has a tapered side wall 57. Both side walls 57 may be tapered. In a desired configuration, opposed side walls 57 are angled relative to one another between approximately 90° and 175°, desirably at approximately 135° relative to one another. To further ensure that radially elastic member 60 disengages from interior annular groove 39 and not exterior annular groove 53, exterior annular groove 53 is desirably deeper than interior annular groove 39. In a desired configuration, interior annular groove 39 and radially elastic member 60 are configured such that the force required to disengage radially elastic member 60 from interior annular groove 39 is less than the friction force such that the syringe assembly 12 is removed without separating syringe housing 26 from plunger 20.

While specific force values are utilized herein, such values are for illustrative purposes only and are not intended to be limiting. Other configurations with different associated force values are within the scope of the invention.

Figure 9:
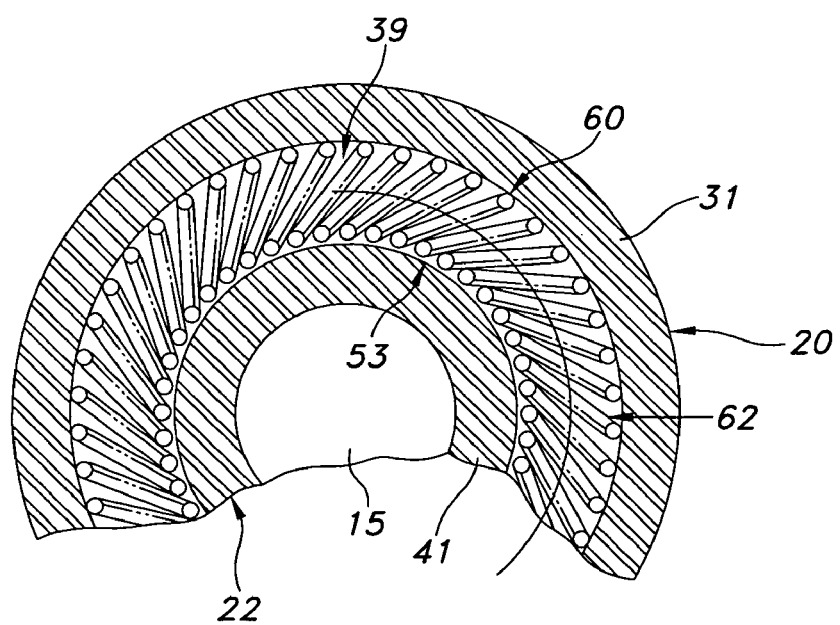
FIG. 9 is a cross-sectional view along the line 9-9 in FIG. 8.

In the present embodiment, radially elastic member 60 is a canted coil spring 62, as shown in FIG. 9. An illustrative canted coil spring is described in U.S. Pat. No. 4,655,462, which is incorporated herein in its entirety. Canted coil spring 62 includes a plurality of coil means, with each of the coil means being interconnected with one another in a spaced-apart relationship and disposed at a preselected acute angle with a centerline of coiled spring 62. As a result, canted coiled spring 62 exerts a constant force in a loading direction approximately normal to the centerline in response to deflection of the coiled spring along the loading direction. While canted coil spring 62 is shown and described herein, other radially elastic members 60, for example, a solid ring made from elastomeric material, may be utilized.

Figure 10:
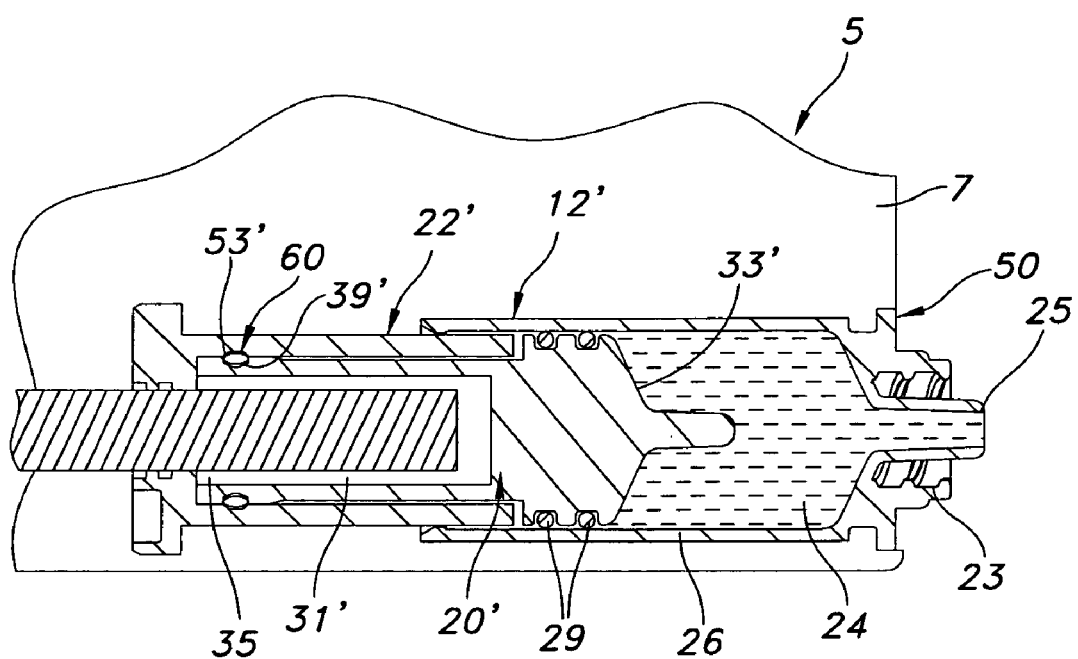
FIG. 10 is a cross-sectional view illustrating an alternative syringe assembly loaded in an operational position within the infusion pump.

Referring to FIG. 10, an alternative embodiment of the present invention is shown. The present embodiment is similar to the previous embodiment, except that plunger 20' of syringe assembly 12' includes an exterior annular groove 39' while drive piston 22' includes an interior annular groove 53'. Rear end 35' of plunger body 31' is configured to be received within drive piston 22' and forward end 33' forms a head. Seal rings 29 or the like are provided between the head and syringe housing 26. Radially elastic member 60 is retained in interior annular groove 53' and is engagable with exterior annular groove 39' to axially secure plunger 20' relative to drive piston 22'. In other aspects, the infusion pump assembly generally operates as in the previous embodiments.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An infusion pump assembly comprising:
   an insulin pump including a drive piston having a radially elastic member associated therewith;
   a syringe assembly including a substantially hollow syringe housing and a plunger axially movable within the syringe housing to expel a fluid therefrom, the plunger having a body with a portion configured to engage the radially elastic member associated with the drive piston such that the plunger is releasably axially secured relative to the drive piston; and
   wherein the plunger body includes a first annular groove configured to receive a portion of the radially elastic member and the drive piston includes a second annular groove configured to receive a portion of the radially elastic member and at least a portion of the plunger body is configured to be received within a portion of the drive piston and the first annular groove is an exterior groove and the second annular groove is an internal groove.

2. The infusion pump assembly of claim 1 wherein the first and second annular grooves are axially aligned when the plunger is positioned in a final assembled position relative to the drive piston.

3. The infusion pump assembly of claim 1 wherein the first annular groove has opposed side walls which are angled relative to one another by approximately 90 to 175 degrees.

4. The infusion pump assembly of claim 1 wherein the interior annular groove has opposed side walls which are angled relative to one another by approximately 135 degrees.

5. The infusion pump assembly of claim 1 wherein the second annular groove is radially deeper than the first annular groove.

6. The infusion pump assembly of claim 1 wherein the radially elastic member is a canted coil spring.

7. The infusion pump assembly of claim 1 wherein the radially elastic member is a solid ring manufactured from an elastomeric material.

* * * * *